United States Patent
Alinski et al.

(10) Patent No.: US 10,251,470 B1
(45) Date of Patent: Apr. 9, 2019

(54) HEAD FOR AN ORAL CARE IMPLEMENT AND ORAL CARE IMPLEMENT

(71) Applicant: The Procter & Gamble Company, Cincinnati, OH (US)

(72) Inventors: Jens Alinski, Kelkheim (DE); Sven Alexander Franke, Darmstadt (DE); Karen Lynn Claire-Zimmet, Taunus (DE); Uwe Jungnickel, Taunus (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 15/729,261

(22) Filed: Oct. 10, 2017

(51) Int. Cl.
| | |
|---|---|
| *A46B 9/02* | (2006.01) |
| *A46B 9/04* | (2006.01) |
| *A46B 5/00* | (2006.01) |
| *A61C 17/22* | (2006.01) |
| *A46B 9/06* | (2006.01) |

(52) U.S. Cl.
CPC ............ *A46B 9/028* (2013.01); *A46B 5/0095* (2013.01); *A46B 9/02* (2013.01); *A46B 9/025* (2013.01); *A46B 9/04* (2013.01); *A46B 9/06* (2013.01); *A61C 17/222* (2013.01)

(58) Field of Classification Search
CPC ........... A46B 9/02; A46B 9/025; A46B 9/028; A46B 9/04
See application file for complete search history.

(56) References Cited

U.S. PATENT DOCUMENTS

| | | | |
|---|---|---|---|
| 1,773,969 | A | 8/1930 | Dreyfus et al. |
| 2,317,485 | A | 4/1943 | Rider |
| 2,876,477 | A | 3/1959 | Stewart |
| 3,032,230 | A | 5/1962 | Gerber |

(Continued)

FOREIGN PATENT DOCUMENTS

| | | |
|---|---|---|
| CN | 200998006 | 1/2008 |
| CN | 202666559 | 1/2013 |

(Continued)

OTHER PUBLICATIONS

International Search Report and Written Opinion of the International Searching Authority, PCT/US2017/035188, dated Sep. 13, 2017, 10 pages.

*Primary Examiner* — Randall Chin
(74) *Attorney, Agent, or Firm* — Vladimir Vitenberg (57) ABSTRACT

A head for an oral care implement has an outer rim and an inner portion. The head comprises at least one tuft of filaments of a first type and at least one tuft of filaments of a second type. The at least one tuft of the first type is arranged at the inner portion of the head and comprises a plurality of filaments, each filament having a longitudinal axis and a substantially circular cross-sectional area extending in a plane substantially perpendicular to the longitudinal axis. The at least one tuft of the second type is arranged at the outer rim of the head and comprises a plurality of filaments, each filament having a longitudinal axis and a substantially cross-shaped cross-sectional area extending in a plane substantially perpendicular to the longitudinal axis, (Continued)

the cross-shaped cross-sectional area having four projections and four channels, the projections and channels being arranged in an alternating manner. The at least one tuft of filaments of the second type has a packing factor within a range from about 40% to about 55%.

14 Claims, 6 Drawing Sheets

(56) References Cited

U.S. PATENT DOCUMENTS

| | | | |
|---|---|---|---|
| 3,072,944 | A | 1/1963 | Clayton |
| 3,214,777 | A | 11/1965 | Kutik |
| 3,238,553 | A | 3/1966 | Bailey et al. |
| 3,302,230 | A | 2/1967 | Poppelman |
| 3,344,457 | A | 10/1967 | Grobert |
| 3,613,143 | A | 10/1971 | Muhler et al. |
| 3,689,118 | A | 9/1972 | Charvat et al. |
| 3,691,585 | A | 9/1972 | Flom |
| 4,167,794 | A | 9/1979 | Pomeroy |
| 4,802,255 | A | 2/1989 | Breuer et al. |
| D301,397 | S | 9/1989 | Lacher |
| 4,958,402 | A | 9/1990 | Weihrauch |
| 5,313,909 | A | 5/1994 | Tseng et al. |
| 5,396,678 | A | 3/1995 | Bredall et al. |
| 5,701,629 | A | 12/1997 | O'Brien |
| 5,806,127 | A | 9/1998 | Samoil et al. |
| 5,906,834 | A | 5/1999 | Tseng |
| 5,985,450 | A | 11/1999 | Keller |
| 6,018,840 | A | 2/2000 | Guay et al. |
| 6,065,176 | A | 5/2000 | Watanabe et al. |
| 6,086,373 | A | 7/2000 | Schiff et al. |
| 6,138,314 | A | 10/2000 | Schiffe et al. |
| 6,276,021 | B1 * | 8/2001 | Hohlbein ............ A46B 9/04 |
| | | | 15/167.1 |
| 6,280,113 | B1 | 8/2001 | Gueret |
| 6,327,736 | B1 | 12/2001 | Schaefer et al. |
| 6,352,772 | B1 | 3/2002 | Keller |
| 6,390,708 | B1 | 5/2002 | Gueret |
| 6,669,389 | B2 | 12/2003 | Gueret |
| RE38,646 | E | 11/2004 | Gueret |
| 6,871,373 | B2 | 3/2005 | Driesen et al. |
| 7,014,800 | B2 | 3/2006 | Weihrauch |
| 7,644,466 | B2 | 1/2010 | Weihrauch et al. |
| 8,297,710 | B2 | 10/2012 | Sakurai et al. |
| 8,453,288 | B2 | 6/2013 | Driesen et al. |
| 8,726,448 | B2 | 5/2014 | Kato et al. |
| 9,445,660 | B2 | 9/2016 | Mintel et al. |
| 2002/0164192 | A1 | 11/2002 | Gueret |
| 2003/0044604 | A1 | 3/2003 | Weihrauch |
| 2003/0088935 | A1 | 5/2003 | Favagrossa |
| 2007/0289078 | A1 | 12/2007 | Driesen et al. |
| 2008/0245385 | A1 | 10/2008 | Schrepf |
| 2009/0142125 | A1 * | 6/2009 | Henrikson ............ A45D 34/045 |
| | | | 401/129 |
| 2010/0306944 | A1 | 12/2010 | Herzog |
| 2012/0246857 | A1 | 10/2012 | Kato et al. |
| 2012/0301210 | A1 | 11/2012 | Sturgis et al. |
| 2013/0318732 | A1 | 12/2013 | Mintel et al. |
| 2015/0150367 | A1 | 6/2015 | Moskovich |
| 2015/0257520 | A1 | 9/2015 | Storkel et al. |
| 2015/0359326 | A1 | 12/2015 | Chan et al. |
| 2015/0361590 | A1 | 12/2015 | Chan et al. |
| 2016/0015163 | A1 | 1/2016 | Newman et al. |

FOREIGN PATENT DOCUMENTS

| | | |
|---|---|---|
| CN | 202941618 | 5/2013 |
| DE | 102006035156 | 1/2008 |
| EP | 0663162 | 7/1995 |
| EP | 2918191 A1 | 9/2015 |
| JP | H06217830 | 8/1994 |
| JP | H06233709 | 8/1994 |
| JP | 200169829 A | 6/2001 |
| JP | 2001169829 | 6/2001 |
| JP | 2002010831 | 1/2002 |
| JP | 2005185399 A | 7/2005 |
| JP | 2005253713 | 9/2005 |
| JP | 2006255068 | 9/2006 |
| JP | 2007068954 | 3/2007 |
| JP | 2007185464 | 7/2007 |
| JP | 2007229317 | 9/2007 |
| JP | 2007283443 | 11/2007 |
| JP | 2007283444 | 11/2007 |
| JP | 2008023205 | 2/2008 |
| JP | 2008212510 | 9/2008 |
| JP | 2009148507 | 9/2009 |
| JP | 2009219520 | 10/2009 |
| JP | 2011030891 | 2/2011 |
| JP | 2012106308 | 6/2012 |
| JP | 3186567 U | 10/2013 |
| KR | 200183557 | 5/2000 |
| KR | 20080011846 | 2/2008 |
| WO | WO200228222 | 4/2002 |
| WO | WO2012096700 | 7/2012 |
| WO | WO2012096701 | 7/2012 |

* cited by examiner

HEAD FOR AN ORAL CARE IMPLEMENT AND ORAL CARE IMPLEMENT

FIELD OF THE INVENTION

The present disclosure is concerned with a head for an oral care implement, the head comprising at least one tuft of a first type and least one tuft of a second type. The tuft of the first type comprises a plurality of filaments with a substantially circular cross-sectional area and is arranged at an inner portion of the head, while the tuft of the second type comprises a plurality of filaments having a cross-shaped cross-sectional area and is arranged at an outer rim of the head. The present disclosure is further concerned with an oral care implement comprising such head.

BACKGROUND OF THE INVENTION

Tufts composed of a plurality of filaments for oral care implements, like manual and powered toothbrushes, are well known in the art. Generally, the tufts are attached to a bristle carrier of a head intended for insertion into a user's oral cavity. A grip handle is usually attached to the head, which handle is held by the user during brushing. The head is either permanently connected or repeatedly attachable to and detachable from the handle.

In order to clean teeth effectively, appropriate contact pressure has to be provided between the free ends of the filaments and the teeth. Generally, the contact pressure depends on the bending stiffness and the displacement of the filaments, while the bending stiffness of a single filament depends on its length and cross sectional area. Usually, filaments with greater length show lower bending stiffness as compared to shorter filaments. However, relatively thin filaments tend to flex away easily and the relatively low bending stiffness results in reduced plaque removal efficiency on teeth surfaces, as well as in less interdental penetrations properties and cleaning performance. In order to compensate said reduction in bending stiffness of longer filaments, the size of the cross sectional area of a filament could be increased. However, relatively thick filaments may create an unpleasant brushing sensation and tend to injure the gums in the oral cavity. In addition, thicker filaments may show reduced bend recovery and usage of said filaments may generate a worn-out impression of the tuft pattern after a relatively short time of use.

Further, filaments having a profile along their length extension resulting in a non-circular cross sectional area, e.g. a polygonal- or a cross-shaped cross sectional area, are also known in the art. Such filaments should improve cleaning properties of oral care implements during normal use. In particular, the profiled edges should provide a stronger scraping action during a brushing process to improve removal of plaque and other residuals on the teeth surfaces.

While toothbrushes comprising conventional type of tufts clean the outer buccal face of teeth adequately, they are generally not as well suited to provide adequate removal of plaque and debris from the interproximal areas and other hard to reach regions of the mouth since penetration into interdental spaces is still relatively difficult. In particular, they are not well suited to sufficiently clean the gingival margin where typically plaque starts to grow. Thus, in order to achieve and preserve good oral health, and to prevent gingivitis, it is important to clean along the gum line and, in particular, the gap between teeth and periodontium, the so called gingival groove. It is known that a lack of good removal of plaque in the gingival groove can cause gingivitis, i.e. inflammation of the gum tissue. Additionally, standard tufts do not provide sufficient capillary effects to remove plaque and debris from the teeth and gum surfaces during brushing. However, in order to achieve good cleaning results, the plaque must be reached by the tufts/filaments, then the plaque must be disrupted and, finally, taken away. Further, the tufts shall provide good sensory feeling on the gums during brushing.

It is an object of the present disclosure to provide a head for an oral care implement which overcomes at least one of the above-mentioned drawbacks. It is also an object of the present disclosure to provide an oral care implement comprising such head.

SUMMARY OF THE INVENTION

In accordance with one aspect, a head for an oral care implement is provided, the head having an outer rim and an inner portion, the head comprising at least one tuft of filaments of a first type and at least one tuft of filaments of a second type, the at least one tuft of the first type being arranged at the inner portion of the head, and comprising a plurality of filaments, each filament having a longitudinal axis and a substantially circular cross-sectional area extending in a plane substantially perpendicular to the longitudinal axis, and the at least one tuft of the second type being arranged at the outer rim of the head, and comprising a plurality of filaments, each filament having a longitudinal axis and a substantially cross-shaped cross-sectional area extending in a plane substantially perpendicular to the longitudinal axis, the cross-shaped cross-sectional area having four projections and four channels, the projections and channels being arranged in an alternating manner, wherein the at least one tuft of filaments of the second type has a packing factor within a range from about 40% to about 55%.

In accordance with one aspect an oral care implement is provided that comprises such head.

BRIEF DESCRIPTION OF THE DRAWINGS

The invention is described in more detail below with reference to various embodiments and figures, wherein.

DETAILED DESCRIPTION OF THE INVENTION

The head according to the present disclosure comprises at least one tuft of a first type being arranged at an inner portion of the head, and at least one tuft of a second type which is arranged at an outer rim of the head, i.e. in close proximity to said outer rim. The at least one tuft of the first type comprises a plurality of filaments having a longitudinal axis and a substantially circular cross-sectional area extending in a plane substantially perpendicular to the longitudinal axis. The at least one tuft of the second type comprises a plurality of filaments, each of said filaments has a longitudinal axis and a substantially cross-shaped cross-sectional area extending in a plane substantially perpendicular to the longitudinal axis. The cross-shaped cross-sectional area has four projections and four channels being arranged in an alternating manner. The longitudinal axis of a filament is defined by the main extension of the filament. In the following, the extension of the filament along its longitudinal axis may also be referred to as the "longitudinal extension of the filament".

The filaments of the at least one tuft of the second type are provided with a relatively low packing factor within a range from about 40% to about 55%, or within a range from about 45% to about 50%. In the context of this disclosure the term "packing factor" is defined as the sum total of the transverse cross-sectional areas of the filaments in the tuft hole divided by the transverse cross-sectional area of the tuft hole. In embodiments where anchors, such as staples, are used to mount the tuft within the tuft hole, the area of the anchoring means is excluded from the transverse cross-sectional area of the tuft hole.

A packing factor of about 40% to about 55%, or from about 45% to about 50%, or about 49% opens up a specific void volume within the tuft while the filaments have still contact to each other along a portion of the outer lateral surface. The void volume may deliver more toothpaste to the tooth brushing process, and the toothpaste can interact with the teeth for a longer period of time which contributes to improved tooth brushing effects. In addition, the void volume, i.e. the space between filaments, enables increased uptake of loosened plaque due to improved capillary action. In other words, such low packing factor may result in more dentifrice/toothpaste retaining at/adhering to the filaments for a longer period of time during a tooth brushing process. Further, the lower tuft density may avoid that the dentifrice spread away which may result in an improved overall brushing process. Toothpaste can be better received in the cannels and, upon cleaning contact with the teeth, directly delivered, whereby a greater polishing effect is achieved, which is desirable, in particular for removal of tooth discoloration.

A relatively low packing factor within a range from about 40% to about 55%, or from about 45% to about 50%, or about 49% may provide improved brushing effectiveness, i.e. better removal of plaque and debris from the teeth's surface and gums due to improved capillary effects. These capillary effects may enable the dentifrice to flow towards the tip/free end of the filaments and, thus, may make the dentifrice more available to the teeth and gums during brushing. At the same time uptake of plaque and debris away from the teeth and gum surfaces is improved.

Further, due to the cross-shaped geometry of the filament, each single filament is stiffer than a circular-shaped filament, when made of the same amount of material. However, due to the low packing factor within a range from about 40% to about 55%, or from about 45% to about 50%, or about 49%, the stiffness of the overall tuft made of cross-shaped filaments is reduced as compared to a tuft of circular-shaped filaments. Surprisingly, it has been found out that such tuft provides improved sensory experience, i.e. a softer feeling within the mouth during brushing, while providing increased cleaning efficiency.

Since the at least one tuft of the second type is arranged at the outer rim of the head, i.e. at the outer edge of the bristle field, said tuft is directed to the gum line, and, thus, can easily engage with the gingival margin and clean the gingival groove thoroughly, where typically plaque starts to grow. In other words, the cleaning along the gum line is significantly improved while a superior sensory brushing effect, i.e. a gentle brushing sensation, is provided for the user. A head for an oral care implement is provided which delivers a targeted cleansing along the most critical and sensitive areas in the mouth, i.e. along the gum line. The projections of the cross-shaped filaments can easily enter the gingival groove, scratch on the surfaces to loosen the plaque, and due to the improved capillary effects of the overall tuft, the plaque can be better taken away. Due to the special shape cross-shaped filaments can penetrate deeper into the gingival groove. In addition, the relatively low packing factor of the tuft of the second type enables the individual cross-shaped filaments to better adapt to the contour of the gum line and gingival grove. At the same time the at least one tuft of the first type made of circular filaments can provide a scrubbing effect on the outer tooth surfaces to clean the substantially flat and less sensitive tooth surfaces adequately.

A plurality of tufts of the first type may be arranged in a row at the inner portion of the head, and a plurality of tufts of the second type may be arranged in a row at the outer rim of the head. Such a tuft configuration may further enhance the cleaning effects as described above.

Each channel of the filaments of the at least one tuft of the second type may have a concave curvature formed by neighboring and converging projections. Said concave curvature may have a radius being within a range from about 0.025 mm to about 0.10 mm, or from about 0.03 mm to about 0.08 mm, or from about 0.04 mm to about 0.06 mm. In other words, two neighboring projections, i.e. two neighboring side lateral edges of said projections may converge at the bottom of a channel and define a "converging region". The neighboring projections may converge in said converging region in a manner that a concave curvature, i.e. with an inwardly curved radius is formed at the bottom of the channel. A radius within such range is relatively large as compared to standard cross-shaped filaments (cf. FIG. 3 and as further described below).

Figure 3:
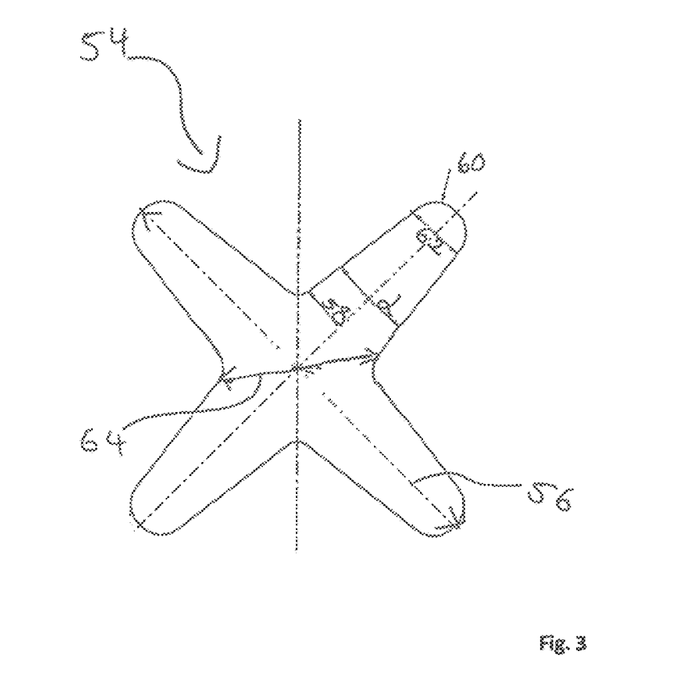
FIG. 3 shows a schematic cross-sectional view of a filament according to the state of the art.

In the past it has been observed that conventional cross-shaped filaments (e.g. as shown in FIG. 3 and further described below) have the disadvantage that these type of filaments can easily catch amongst themselves, both during manufacturing and brushing. However, it has been surprisingly found out that the specific geometry/contour of the outer surface of the filament according to the present disclosure allows for improved manufacturability since there is significant less likelihood that the filaments get caught when a plurality of said filaments is combined to form one tuft during a so-called "picking process".

Further, due to the relatively large radius at the bottom of the channel, the filament is provided with increased stability, and, thus, less filament damage occur during the brush manufacturing process, e.g. when the filaments get picked and fixed on the mounting surface of the brush head during a stapling or hot tufting process. In the past, it has been observed that a relatively high number of conventional cross-shaped filaments get damaged during the picking process, in particular projections may break away from the filament, or the filament gets spliced in the converging region at the bottom of a channel. Spliced filaments can provide relatively sharp edges which may harm/injure the oral tissue during brushing.

Further, surprisingly it has been found out that due to the specific geometry of the radius of the concave curvature, the filaments within a tuft can be better packed with a relatively low packing factor, i.e. within a range from about 40% to about 55%, as gaps between two adjacent filaments can be maximized. It has been found out that it is important that the filaments open up a specific void area while still having contact to each other. In order to produce a toothbrush that is compliant with regulatory requirements and appreciated by the consumer regarding the overall appearance, typically a high packing factor (about 70% to about 80% for round filaments; about 80% for diamond-shaped filaments; about 89% for trilobal filaments) is needed. With respect to toothbrushes manufactured by a stapling process, a packing factor lower than about 70% results in insufficiently compressed filaments within the tuft hole and, thus, provides insufficient tuft retention. Consequently, regulatory requirements are not met in case round filaments are provided with a packing factor lower than about 70%. For hot tufted toothbrushes, a packing factor lower than about 70% would allow plastic melt entering into the tuft during the over molding process as the pressure of the melt pushes the filaments of the tuft to one side until the filaments have contact to each other. So-called polyspikes are thereby formed which may injure/harm the gums and, thus resulting in unsafe products. Beside regulatory and safety aspects a low packed tuft of round filaments would have a "wild" and destroyed appearance and would not be accepted by consumers. However, with the usage of cross-shaped filaments having a radius of the concave curvature of the channel within a range from about 0.025 mm to about 0.10 mm a low packing factor can be achieved for compliant and safe products having an acceptable overall appearance while providing improved cleaning properties.

Figure 7:
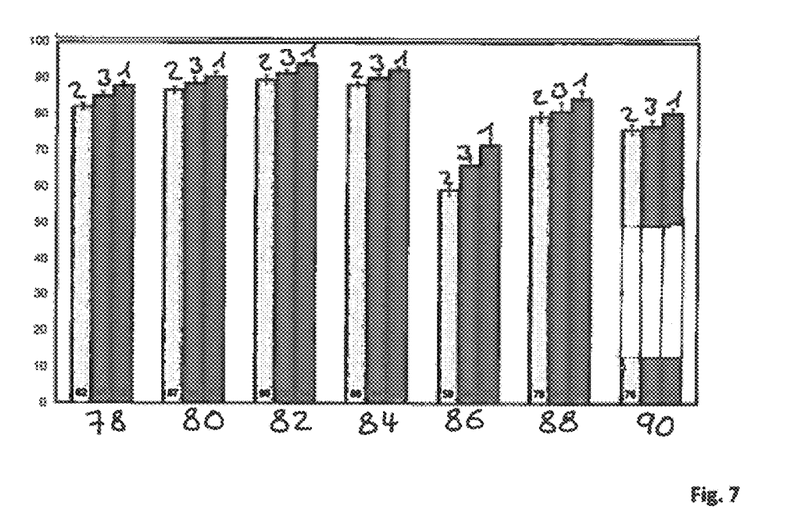
FIG. 7 shows a diagram in which brushing results of a tuft comprising filaments according to FIG. 2 are compared with brushing results of tufts according to two comparative example embodiments.

Each projection of the cross-shaped cross-sectional area comprises two outer lateral edges along the filament's longitudinal extension. These lateral edges may generate relatively high concentrated stress on the tooth surfaces to disrupt and remove plaque. The outer edges can provide a scraping effect so that plaque and other debris get loosened more effectively. Due to the relatively large radius of the concave curvature at the bottom of the channel, the projections are provided with increased stiffness/stability to loosen/remove plaque from the teeth surfaces more easily/effectively. The channels can then capture the disrupted plaque and may move it away from the teeth. As shown in FIG. 7 and further explained below, a tuft comprising a plurality of filaments according to the present disclosure provides improved plaque removal from the buccal, lingual, occlusal and interdental surfaces as well as along the gum line as compared to a tuft of circular or conventional cross-shaped filaments.

The cross-shaped cross sectional area of each filament of the tuft of the second type may have an outer diameter. In the context of the present disclosure the outer diameter is defined by the length of a straight line that passes through the center of the filament's cross-sectional area and whose endpoints lie on the most outer circumference of the cross-sectional area. In other words, the cross-shaped cross-sectional area has an imaginary outer circumference in the form of a circle (i.e. outer envelope circle), and the outer diameter is defined as the longest straight line segment of the circle passing through the center of the circle.

The outer diameter may be within a range from about 0.15 mm to about 0.40 mm, or from about 0.19 mm to about 0.38 mm, or the outer diameter may be within a range from about 0.22 mm to about 0.35 mm, or from about 0.24 mm to about 0.31 mm.

The ratio of the outer diameter to the radius of the curvature of the channel may be within a range from about 2.5 to about 12. Alternatively, the ratio of the outer diameter to the radius of the curvature of the channel may be within a range from about 2.7 to about 9.

Surprisingly, it has been found out that such filament geometry provides even further improved cleaning performance while maintaining brush comfort in the mouth. In addition, it has been found out that such geometry helps even more to reduce the appearance of filament/tuft wear since there is even less likelihood that the filaments get caught during brushing. Further, the manufacturability of such filaments during a toothbrush manufacturing process is further improved.

Each projection of the cross-shaped cross-sectional area of the filaments of the tuft of the second type may be end-rounded thereby forming a curvature. Said curvature may have a diameter. The diameter of the curvature of the projection may be within a range from about 0.01 mm to about 0.04 mm, or within a range from about 0.018 mm to about 0.026 mm.

The ratio of the diameter of the curvature of the projection to the radius of the curvature of the channel may be within a range from about 0.2 to about 1.5, or from about 0.3 to about 1.0, or from about 0.5 to about 0.7. Said ratio is relatively low as compared to standard cross-shaped filaments according to the state of the art (cf. FIG. 3 and as further described below). In other words, the radius of the concave curvature of the channel is relatively large with respect to the diameter of the curvature of the projection, i.e. with respect to the width extension of the projection—or in other words, the diameter of the curvature of the projection can be relatively thin as compared to the radius of the concave curvature of the channel. The relatively large radius provides the relatively thin projections with increased stability. Thus, there is less likelihood that the filaments/projections get damaged or that the relatively thin projections break away during the brush manufacturing process, in particular when the filaments get picked. In other words, the manufacturability of such filaments during a toothbrush manufacturing process is further improved.

Further, surprisingly, it has been found out that such filament geometry provides even further improved cleaning performance while maintaining brush comfort in the mouth. In addition, it has been found out that such geometry further helps to reduce the appearance of filament/tuft wear since there is even less likelihood that the filaments get caught during brushing.

The diameter of the curvature of the projection may be within a range from about 6% to about 15% or from about 8% to about 12% of the outer diameter of the filament. Surprisingly it has been found out that such filaments may adapt to the teeth contour in an even better manner and penetrate into the interdental spaces more easily to remove plaque and debris more completely.

The projections of the cross-shaped filament may taper radially off in an outward direction, i.e. in a direction away from the center of the cross-sectional area and towards the outer circumference. Such tapered projections may further assure access to narrow spaces and other hard to reach areas and may be able to penetrate into/enter interdental areas even more deeply and effectively. Since the bending stiffness of a cross-shaped filament is higher as compared to a circular-shaped filament made of the same amount of material, the higher bending stiffness may force the filament's projections to slide into the interdental areas more easily.

The projections may taper radially outwards by an angle within a range from about 6° to about 25°, or by an angle within a range from about 8° to about 20°. Surprisingly, it has been found out that such tapering allows for optimal interdental penetration properties. Additionally, such filament can be more easily bundled in a tuft without catching on contours of adjacent filaments.

The filaments of the tuft of the second type may be a substantially cylindrical filament, i.e. the filament may have a substantially cylindrical outer lateral surface. In other words, the shape and size of the cross-sectional area of the filament along its longitudinal axis may not vary substantially, i.e. the shape and size of the cross-sectional area may be substantially constant over the longitudinal extension of the filament. In the context of this disclosure the term "outer lateral surface of a filament" means any outer face or surface of the filament on its sides. This type of filament may provide increased bending stiffness as compared to tapered filaments. A higher bending stiffness may further facilitate the filament to penetrate into interdental gaps/spaces. Further, cylindrical filaments are generally slowly worn away which may provide longer lifetime of the filaments.

The cylindrical filament may have a substantially end-rounded tip/free end to provide gentle cleaning properties. End-rounded tips may avoid that gums get injured during brushing. Within the context of this disclosure, end-rounded filaments would still fall under the definition of a substantially cylindrical filament.

Alternatively, the filaments of the tuft of the second type may comprise along its longitudinal axis a substantially cylindrical portion and a tapered portion, the tapered portion tapers in the longitudinal direction towards a free end of the filament, and the cylindrical portion has a cross-sectional area according to the present disclosure. In other words, the filaments of the tuft of the second type may be tapered filaments having a pointed tip. Tapered filaments may achieve optimal penetration into areas between two teeth as well as into gingival pockets during brushing and, thus, may provide improved cleaning properties. The tapered filaments may have an overall length extending above the mounting surface of the head within a range from about 8 mm to about 16 mm, optionally about 12.5 mm, and a tapered portion within a range from about 5 mm to about 10 mm measured from the tip of the filament. The pointed tip may be needle shaped, may comprise a split or a feathered end. The tapering portion may be produced by a chemical and/or mechanical tapering process.

The filaments of the tufts of the first and/or second type may be made of polyamide, e.g. nylon, with or without an abrasive such as kaolin clay, polybutylene terephthalate (PBT) with or without an abrasive such as kaolin clay and/or of polyamide indicator material, e.g. nylon indicator material, colored at the outer surface. The coloring on the polyamide indicator material may be slowly worn away as the filament is used over time to indicate the extent to which the filament is worn.

The filaments of the tufts of the first and/or second type may comprise at least two segments of different materials. At least one segment may comprise a thermoplastic elastomer material (TPE) and at least one segment may comprise polyamide, e.g. nylon, with or without an abrasive such as kaolin clay, polybutylene terephthalate (PBT) with or without an abrasive such as kaolin clay or a polyamide indicator material, e.g. a nylon indicator material, colored at the outer surface. These at least two segments may be arranged in a side-by-side structure or in a core-sheath structure which may result in reduced stiffness of the overall filament. A core-sheath structure with an inner/core segment comprising a harder material, e.g. polyamide or PBT, and with an outer/sheath segment surrounding the core segment and comprising a softer material, e.g. TPE, may provide the filament with a relatively soft outer lateral surface which may result in gentle cleaning properties.

The filaments of the tufts of the first and/or second type may comprise a component selected from fluoride, zinc, strontium salts, flavor, silica, pyrophosphate, hydrogen peroxide, potassium nitrate or combinations thereof. For example, fluoride may provide a mineralization effect and, thus, may prevent tooth decay. Zinc may strengthen the immune system of the user. Hydrogen peroxide may bleach/whiten the teeth. Silica may have an abrasive effect to remove dental plaque and debris more effectively. Pyrophosphate may inhibit the formation of new plaque, tartar and dental calculus along the gum line. A filaments comprising pyrophosphate may offer lasting protection against inflammations of the gums and mucous membrane of the mouth.

If a plurality of such filaments is bundled together to form a tuft, they may be arranged in a manner that filaments at the tuft's outer lateral surface may comprise pyrophosphate to inhibit the formation of plaque, tartar and dental calculus along the gum line whereas filaments arranged in the center of the tuft may comprise fluoride to mineralize the teeth during a brushing process.

At least one of the components listed above may be coated onto a sheath, i.e. onto an outer segment of a filament. In other words, at least some of the filaments of the tuft may comprise a core-sheath structure wherein the inner/core segment may comprise TPE, polyamide or PBT, and the outer/sheath segment may comprise at least one of the components listed above. Such core-sheath structure may make the component(s) directly available to the teeth in a relatively high concentration, i.e. the component(s) may be in direct contact with the teeth during brushing.

Alternatively, at least one of the components listed above may be co-extruded with TPE, polyamide, e.g. nylon, and/or PBT. Such embodiments may make the component(s) gradually available to the teeth when the filament material is slowly worn away during use.

The at least one tuft of the second type attached to the head for an oral care implement may have a longitudinal axis and a cross-sectional area which extends in a plane that is perpendicular to said longitudinal axis. The plurality of filaments may be arranged in a manner that the cross-sectional area of the tuft has a scaled up shape of the respective shape of each individual filament which makes up the tuft. In other words, the tuft is a scaled up version of its filaments, i.e. the shape of the cross-sectional area of the tuft may have substantially the same cross-shaped cross-sectional area as each individual filament but in a larger size. The shape of the cross-sectional area of the tuft may correspond to the shape of the cross-sectional area of its filaments. In the context of this disclosure the term "cross-sectional area having a scaled up shape" means a cross-sectional area comprising the same shape but in increased size. In other words, the type of shape may be the same but the size of the cross-sectional area is different, i.e. increased. Any gaps, irregularities, reliefs or slots which may be present between two adjacent individual filaments at the outer circumference of the cross-sectional area of the tuft do not contribute to the substantial shape of said cross-sectional area and are, thus, to be neglected.

Such tuft may provide increased cleaning properties. As outlined above, the specific shape/geometry of the individual filaments has specific cleaning properties which differ from the properties of regular filaments with a circular cross-sectional area. These specific cleaning properties may be enhanced by arranging the filaments in a manner so that they form a cross-sectional shape of the overall tuft which is a scaled up version of the cross-sectional shape of each individual filament. In addition, as the specific geometry of each single filament may be generally not visible to the user, the tuft in accordance with the present disclosure may communicate the respective geometry to the user and, thus, the corresponding cleaning properties of the filaments which make up said tuft.

As the filaments and the tuft of the second type, respectively, may have each a cross-sectional area with a non-circular shape, the filaments as well as the overall tuft may provide anisotropic bending stiffness properties during a brushing process. In case a given contact pressure is applied to the free end of the filaments/tuft the amount of deflection/displacement of the filaments/tuft depends on the diameter/radius of the filaments/tuft. The smaller the diameter/radius, the higher is the deflection/displacement of the free end of the filaments/tuft, and vice versa, the larger the diameter/radius, the smaller is the deflection/displacement of the free end of the filaments/tuft. The tuft may be arranged on the mounting surface of the head in a manner that higher bending stiffness is provided in a direction where higher cleaning forces may be needed. Lower bending stiffness may be provided in a direction where gentle cleaning forces or a massaging effect may be required.

The oral care implement according to the present disclosure may be a toothbrush comprising a handle and a head. The head extends from the handle and may be either repeatedly attachable to and detachable from the handle, or the head may be non-detachably connected to the handle. The toothbrush may be an electrical or a manual toothbrush.

The head may comprise a bristle carrier having a substantially circular or oval shape. Such a bristle carrier may be provided for an electrical toothbrush which may perform a rotational oscillation movement. The bristle carrier of an electrical toothbrush can be driven to rotate about and to move axially along an axis of movement in an oscillating manner, wherein such axis of movement may extend substantially perpendicular to the plane defined by the upper top surface of the bristle carrier. The tufts according to the present disclosure may be attached to the bristle carrier. The projections of the filaments of the at least one tuft of the second type may penetrate into interdental areas and hard to reach regions more easily during the rotational oscillation movement of the head which may provide further improved cleaning properties of the head. Plaque and other residues may be loosened by the oscillating action of the filaments being substantially perpendicular to the tooth surfaces, whereas the rotational movement may sweep the plaque and further residues away.

A head for an oral care implement in accordance with the present disclosure may comprise a bristle carrier being provided with tuft holes, e.g. blind-end bores. Tufts according to the present disclosure may be fixed/anchored in said tuft holes by a stapling process/anchor tufting method. This means, that the filaments of the tufts are bent/folded around an anchor, e.g. an anchor wire or anchor plate, for example made of metal, in a substantially U-shaped manner. The filaments together with the anchor are pushed into the tuft hole so that the anchor penetrates into opposing side walls of the tuft hole thereby anchoring/fixing/fastening the filaments to the bristle carrier. The anchor may be fixed in opposing side walls by positive and frictional engagement. In case the tuft hole is a blind-end bore, the anchor holds the filaments against a bottom of the bore. In other words, the anchor may lie over the U-shaped bend in a substantially perpendicular manner. Since the filaments of the tuft are bent around the anchor in a substantially U-shaped configuration, a first limb and a second limb of each filament extend from the bristle carrier in a filament direction. Filament types which can be used/are suitable for usage in a stapling process are also called "two-sided filaments". Heads for oral care implements which are manufactured by a stapling process can be provided in a relatively low-cost and time-efficient manner. Due to the improved geometry of the filaments of the at least one tuft of the second type according to the present disclosure, fewer filaments get damaged, e.g. by slicing, when the filaments get picked and fixed on the mounting surface of the brush head during the stapling process. Further, fewer filaments get caught on the outer surface of a neighboring filament when a plurality of filaments are picked to form one tuft.

Alternatively, the tufts may be attached/secured to the head by means of a hot tufting process. One method of manufacturing the head of an oral care implement may comprise the following steps: Firstly, the tufts may be formed by providing a desired amount of filaments according to the present disclosure. Secondly, the tufts may be placed into a mold cavity so that ends of the filaments which are supposed to be attached to the head extend into said cavity. Thirdly, the head or an oral care implement body comprising the head and the handle may be formed around the ends of the filaments extending into the mold cavity by an injection molding process, thereby anchoring the tufts in the head. Alternatively, the tufts may be anchored by forming a first part of the head—a so called "sealplate"—around the ends of the filaments extending into the mold cavity by an injection molding process before the remaining part of the oral care implement may be formed. Before starting the injection molding process, the ends of the at least one tuft extending into the mold cavity may be optionally melted or fusion-bonded to join the filaments together in a fused mass or ball so that the fused masses or balls are located within the cavity. The tufts may be held in the mold cavity by a mold bar having blind holes that correspond to the desired position of the tuft on the finished head of the oral care implement. In other words, the filaments of the tufts attached to the head by means of a hot tufting process may be not doubled over a middle portion along their length and may be not mounted in the head by using an anchor/staple. The tufts may be mounted on the head by means of an anchor-free tufting process. A hot tufting manufacturing process allows for complex tuft geometries. For example, the tufts may have a specific topography/geometry at its free end, i.e. at its upper top surface, which may be shaped to optimally adapt to the teeth's contour and to further enhance interdental penetration. For example, the topography may be chamfered or rounded in one or two directions, pointed or may be formed linear, concave or convex. Due to the improved geometry of the filaments of the at least one tuft of the second type according to the present disclosure, fewer filaments get damaged, e.g. by slicing, when the filaments get picked and fixed on the mounting surface of the brush head during the hot-tufting process. Further, fewer filaments get caught on the outer surface of a neighboring filament when a plurality of filaments are picked to form one tuft.

The following is a non-limiting discussion of example embodiments of oral care implements and parts thereof in accordance with the present disclosure, where reference to the Figures is made.

Figure 1:
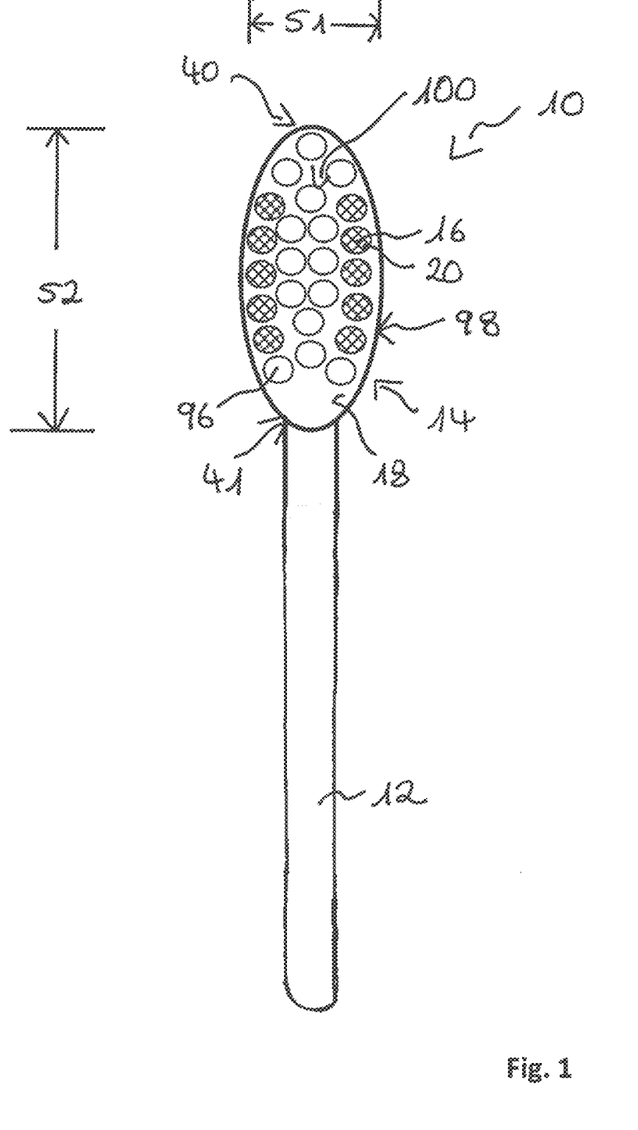
FIG. 1 shows a schematic perspective view of an oral care implement comprising a head according to the present disclosure.
Figure 5:
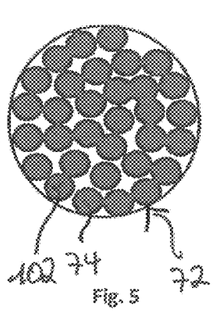
FIG. 5 shows a schematic cross-sectional view of a tuft according to a first comparative example embodiment.

FIG. 1 shows a schematic top-down view of an oral care implement 10 which could be a manual or an electrical toothbrush 10 comprising a handle 12 and a head 14 extending from the handle 12 in a longitudinal direction. The head 14 has a proximal end 41 close to the handle 12 and a distal end 40 furthest away from the handle 12, i.e. opposite the proximal end 41. The head 14 may have substantially the shape of an oval with a length extension 52 and a width extension 51 substantially perpendicular to the length extension 52. A plurality of tufts of the first type 96 comprising a plurality of circular-shaped filaments 74 (e.g. as shown in FIG. 5), and a plurality of tufts of the second type 16 comprising a plurality of cross-shaped filaments 20 may be secured to the head 14 by means of a hot tufting or stapling process. Tufts 16, 96 may extend from a mounting surface 18 of the head 14 in a substantially orthogonal manner. The tufts of the second type 16 are arranged on the mounting surface 18 in rows at the outer rim 98, i.e. in close proximity to the outer rim 98, along the length extension 52 of the head 14. The tufts of the first type 96 are arranged at an inner portion 100 of the head 14, i.e. between the rows of tufts of the second type 16. The tufts of the second type 16 have a packing factor within a range from about 40% to about 55%, or from about 45% to about 50%, or about 49%. The "packing factor" is defined as the total sum of the cross-sectional areas 22 of the filaments 20 divided by the cross-sectional area of the tuft hole.

Figure 2:
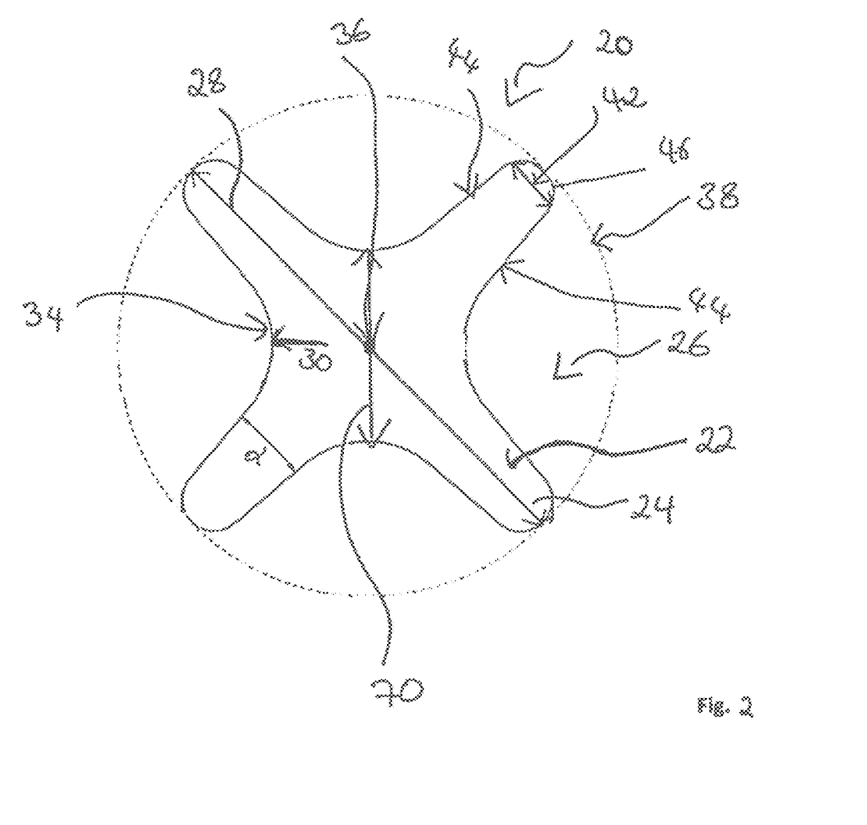
FIG. 2 shows a schematic cross-sectional view of one filament of the tuft of the second type as shown in FIG. 1.

The tufts of the second type 16 as illustrated in FIG. 1 comprise a plurality of end-rounded cross-shaped filaments 20, one of them being shown in FIG. 2. Alternatively, the filaments 20 may be tapered filaments comprising along the longitudinal axis a substantially cylindrical portion and a tapered portion. The tapered portion tapers towards the free end of the filament 20, and the cylindrical portion has a cross-sectional area 22 according to the present disclosure.

FIG. 2 shows a schematic cross-sectional view of a filament 20 of tuft 16. The filament 20 has a longitudinal axis and a substantially cross-shaped cross-sectional area 22 extending in a plane substantially perpendicular to the longitudinal axis. The cross-shaped cross-sectional area 22 has four projections 24 and four channels 26. The projections 24 and channels 26 are arranged in an alternating manner. Each projection 24 tapers in an outward direction by an angle α within a range from about 6° to about 25°, or from about 8° to about 20°.

The cross-sectional area 22 has an outer diameter 28 passing through the center 36 of the filament's cross-sectional area 22. The endpoints of the outer diameter 28 lie on the most outer circumference 38 of the cross-sectional area 22. The outer diameter 28 has a length extension within a range from about 0.15 mm to about 0.40 mm, from about 0.19 mm to about 0.38 mm, from about 0.22 mm to about 0.35 mm, or from about 0.24 mm to about 0.31 mm.

Each channel 26 has a concave curvature 34, i.e. a curvature being curved inwardly towards the center 36 of the cross-sectional area 22. The concave curvature 34 is formed at the bottom of each channel 26 by two neighboring and converging projections 24. The concave curvature 34 has a radius 30 which is in a range from about 0.025 mm to about 0.10 mm, or from about 0.03 mm to about 0.08 mm, or from about 0.04 mm to about 0.06 mm.

The ratio of the outer diameter 28 to the radius 30 of the concave curvature 34 is within a range from about 2.5 to about 12, or from about 2.7 to about 9.

Each projection 24 is end-rounded thereby forming a curvature with a specific diameter 42. Said diameter 42 can also be defined as the width extension 42 extending between two opposite lateral edges 44 of the projection 24. The ratio of the diameter 42 of the curvature of the projection 24 to the radius 30 of the curvature 34 of the channel 26 is within a range from about 0.2 to about 1.5, or from about 0.3 to about 1.0, or from about 0.5 to about 0.7.

Further, the diameter 42 of the end-rounding of the projection 24 is defined in a range from about 6% to about 15%, or from about 8% to about 12% of the outer diameter 28 of the filament 20. For example, the diameter 42 of the end-rounding of the projection 24 may be within a range from about 0.01 mm to about 0.04 mm, or within a range from about 0.018 mm to about 0.026 mm.

FIG. 3 shows a schematic cross-sectional view of a cross-shaped filament 54 according to the state of the art. Filament 54 comprises the following dimensions:
Outer diameter 56: 0.295 mm
Radius 58 of the concave curvature of the channel: 0.01 mm
Ratio outer diameter 56 to radius 58 of the concave curvature: 29.5
Tapering of the projections α: 15°
Diameter 62 of the curvature of the projection: 0.04 mm
Ratio of the diameter 62 to the radius 58: 4
Inner diameter 64: 0.1 mm.

Figure 4:
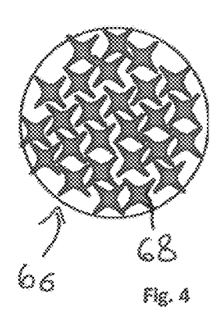
FIG. 4 shows a schematic cross-sectional view of an example embodiment of a tuft of the second type.

FIG. 4 shows a schematic cross-sectional view of a tuft of the second type 66 according to the present disclosure (example embodiment 1). Tuft 66 has a packing factor of about 49%. The filaments 68 of tuft 66 have the following dimensions:
Outer diameter 28: 0.309 mm
Radius 30 of the concave curvature: 0.06 mm
Ratio outer diameter 28 to radius 30 of the concave curvature: 5.15
Tapering of the projections α: 10°
Diameter 42 of the curvature of the projection 42: 0.04 mm
Ratio of the diameter 42 to the radius 30: 0.67
Inner diameter 70: 0.12 mm.

FIG. 5 shows a schematic cross-sectional view of a tuft 72 comprising a plurality of circular filaments 74 according to the state of the art. The diameter of filaments 74 is about 0.178 mm (7 mil). Such tuft 72 has a packing factor of about 77% (comparative example 2).

Figure 6:
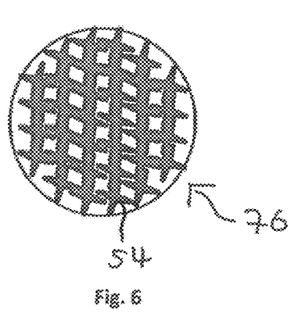
FIG. 6 shows a schematic cross-sectional view of a tuft according to a second comparative example embodiment.

FIG. 6 shows a schematic cross-sectional view of a tuft 76 comprising a plurality of filaments 54 according to FIG. 3. Such tuft 76 has a packing factor of about 58% (comparative example 3).

COMPARISON EXPERIMENTS

Robot Tests:

Tuft 66 (diameter of the tuft: 1.7 mm) in accordance with FIG. 4 comprising a plurality of filaments 68 (example embodiment 1), the tuft 72 (diameter of the tuft: 1.7 mm) according to FIG. 5 comprising a plurality of filaments 74 (comparative example 2), and the tuft 76 (diameter of the tuft: 1.7 mm) according to FIG. 6 comprising a plurality of filaments 54 (comparative example 3) were compared with respect to their efficiency of plaque substitute removal on artificial teeth (typodonts).

Brushing tests were performed using a robot system KUKA 3 under the following conditions (cf. Table 1):

TABLE 1

| Product | program upper jaw | program lower jaw | force | power supply |
|---|---|---|---|---|
| All tested products | EO_IND | EU_INDI | 3 N | no |
| total cleaning time | 60 s | 60 s | | |
| program version | 9.11.09 Eng | 9.11.09 Eng | | |
| SYSTEC speed | 60 | 60 | | |
| SYSTEC amplitude x/y | 20/0 | 20/0 | | |
| number of moves | 3 | 3 | | |
| Movement | horizontal | | | |
| used handle/mould | No/no | | | |

FIG. 7 shows the amount of plaque substitute removal in % of example embodiment 1, comparative example 2 and comparative example 3, each with respect to all tooth surfaces 78, buccal surfaces 80, lingual surfaces 82, lingual and buccal surfaces 84, occlusal surfaces 86, the gum line 88 and interdental surfaces 90.

FIG. 7 clearly shows that example embodiment 1 provides significant improved plaque removal properties with respect all tooth surfaces 78, buccal surfaces 80, lingual surfaces 82, lingual and buccal surfaces 84, occlusal surfaces 86, the gum line 88 and interdental surfaces 90 as compared to comparative examples 2 and 3. The most significant improvement of the cleaning performance occurred on the occlusal surfaces 86 with an improvement of 22% and 9%, respectively.

Figure 8:
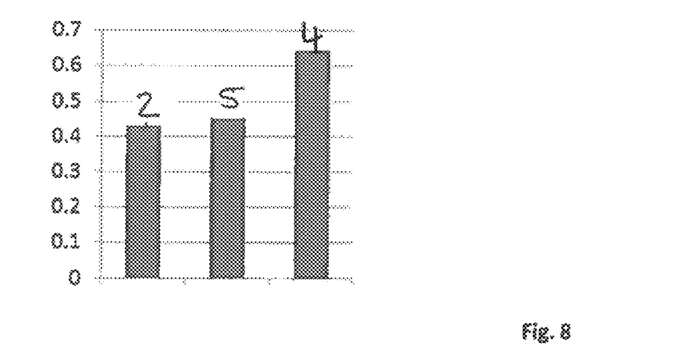
FIG. 8 shows a diagram in which "slurry uptake mass" of a tuft comprising filaments according to FIG. 2 is compared with "slurry uptake mass" of tufts according to two comparative example embodiments.

Slurry Uptake Tests:

FIG. 8 shows a diagram in which "slurry uptake mass" of a tuft of the second type (diameter of the tuft: 1.7 mm) having a packing factor of about 46% (example embodiment 4) is compared with "slurry uptake mass" of a tuft (diameter of the tuft: 1.7 mm) comprising diamond shaped filaments (cf. FIG. 10) and having a packing factor of about 80% (comparative example 5), and with "slurry uptake mass" of the tuft 72 having a packing factor of about 77% according to comparative example 2.

Figure 10:
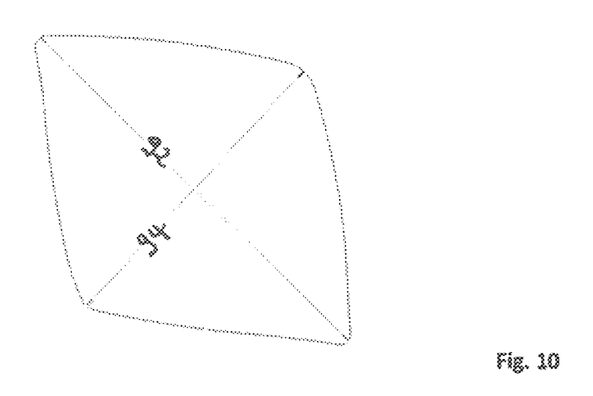
FIG. 10 shows a schematic cross-sectional view of a diamond-shaped filament according to the state of the art.

The filaments of example embodiment 4 have the following dimensions:

Outer diameter: 0.269 mm
Radius of the concave curvature of the channel: 0.05 mm
Ratio of outer diameter to radius of the concave curvature: 5.38
Tapering of the projections α: 14°
Diameter of the curvature of the projection: 0.029 mm
Ratio of the diameter of the curvature of the projection to the radius concave curvature of the channel: 0.58
Inner diameter: 0.102 mm The filaments of comparative example 5 have the following dimensions (cf. FIG. 10):

Longer diagonal length 92: 0.29 mm
Shorter diagonal length 94: 0.214 mm

Figure 9:
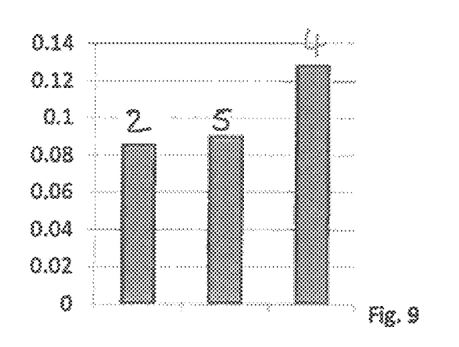
FIG. 9 shows a diagram in which "slurry uptake speed" of a tuft comprising filaments according to FIG. 2 is compared with "slurry uptake speed" of tufts according to two comparative example embodiments.

FIG. 9 shows a diagram in which "slurry uptake speed" of example embodiment 4 is compared with "slurry uptake speed" of comparative examples 2 and 5.

Test Description:

Brush heads comprising tufts according to example embodiment 4 and comparative examples 2 and 5 were fixed in a horizontal position with filaments pointing down. A bowl of toothpaste slurry (toothpaste:water=1:3) was placed with a scale directly under the brush heads. The scale was used to measure the amount of slurry in the bowl. When the test was started, the brushes moved down with 100 mm/s and dipped 2 mm deep into the slurry. Then the brushes were hold for 5 s in the toothpaste slurry and pulled out again with 100 mm/min. The force in vertical direction was measured over time.

FIGS. 8 and 9 clearly show that example embodiment 4 provides significant improved "slurry uptake" in terms of mass and speed as compared to comparative examples 2 and 5. The increased void volume within the tuft of example embodiment 4 enables improved capillary action. This leads to increased uptake of toothpaste (slurry) so that the toothpaste interacts/contributes longer to the tooth brushing process. The tuft of example embodiment 4 can take-up about 50% more toothpaste slurry with about 50% higher uptake speed which results in improved tooth cleaning effects. In other words, besides delivering more toothpaste to the tooth brushing process, the specific void volume within the tuft of example embodiment 4 enables also increased uptake of loosened plaque. This results in an overall improved clinical performance of a toothbrush comprising a head with a tuft configuration according to the present disclosure.

Figure 11:
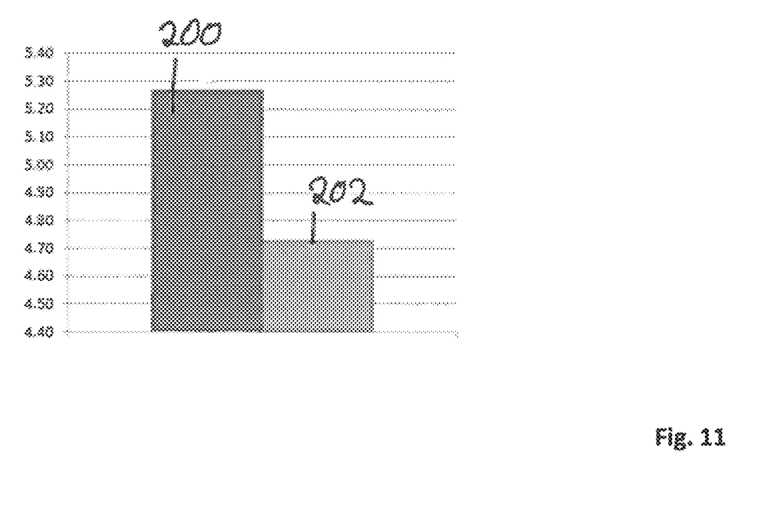
FIG. 11 shows a diagram in which penetration perception under the gum-line of cross-shaped filaments is compared with penetration perception of circular-shaped filaments.

Further, the ability to feel improved filament penetration/reach of cross-shaped filaments under the gum-line was tested via a trained sensory panel comprising 11 panelists. The sensory analysis was performed according to DIN ISO 10967-1 and the assessment was described according to DIN ISO 10964. FIG. 11 clearly shows that brush 200 comprising cross-shaped filaments provided improved feeling of filament penetration under the gum-line in comparison to brush 202 comprising circular-shaped filaments.

Figure 12:
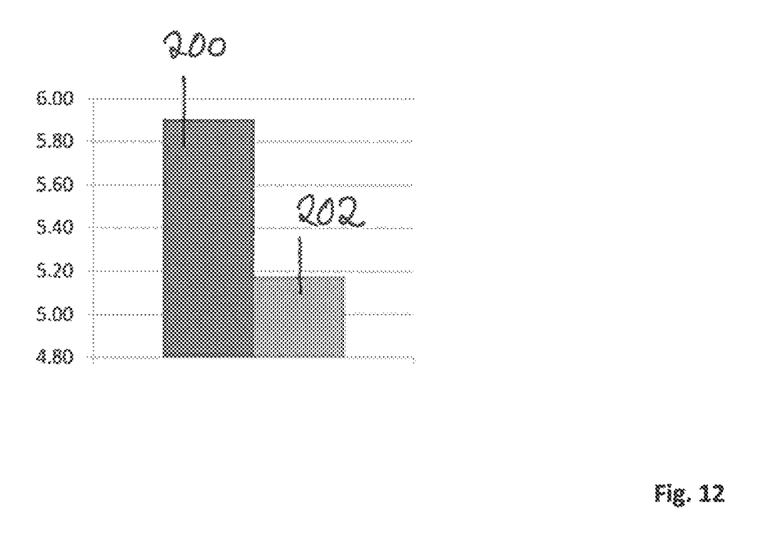
FIG. 12 shows a diagram in which gum massage perception of cross-shaped filaments of FIG. 11 is compared with gum massage perception of the circular-shaped filaments of FIG. 11.

In addition, in the same sensory study it was shown that brush 200 comprising cross-shaped filaments provided improved gum massaging effects as compared to brush 202 (cf. FIG. 12). According to these sensory tests, brush 200 showed both, improved gum massage and penetration perception as compared to brush 202, while not being perceived as being stiffer.

Configurations of brushes 200 and 202:

| | Brush 200 | Brush 202 |
|---|---|---|
| Packing factor of tufts | 52% | 74% |
| Diameter of the tuft | 1.7 mm | 1.7 mm |
| Outer diameter 28 of the filament | 0.308 mm | Combination of tufts comprising filaments with diameter of 0.152 mm, 0.161 mm and 1.178 mm, respectively |
| Radius 30 of the concave curvature | 0.06 mm | |
| Ratio outer diameter 28 to radius 30 of the concave curvature | 5.13 | |
| Tapering of the projections α | 14.4° | |
| Inner diameter 70 | 0.119 mm | |

In the context of this disclosure, the term "substantially" refers to an arrangement of elements or features that, while in theory would be expected to exhibit exact correspondence or behavior, may, in practice embody something slightly less than exact. As such, the term denotes the degree by which a quantitative value, measurement or other related representation may vary from a stated reference without resulting in a change in the basic function of the subject matter at issue.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A head for an oral care implement comprising: the head having an outer rim and an inner portion, the head comprising at least one tuft of filaments of a first type and at least one tuft of filaments of a second type,
   the at least one tuft of the first type being arranged at the inner portion of the head, and comprising a plurality of filaments, each filament having a longitudinal axis and a substantially circular cross-sectional area extending in a plane substantially perpendicular to the longitudinal axis, and
   the at least one tuft of the second type being arranged at the outer rim of the head, and comprising a plurality of filaments, each filament having a longitudinal axis and a substantially cross-shaped cross-sectional area extending in a plane substantially perpendicular to the longitudinal axis, the cross-shaped cross-sectional area having four projections and four channels, the projections and channels being arranged in an alternating manner, wherein
   the at least one tuft of filaments of the second type has a packing factor within a range from about 40% to about 55% wherein each channel of the filaments of the at least one tuft of the second type has a concave curvature formed by neighboring and converging projections, the concave curvature having a radius, and the radius of the concave curvature of the channel is within a range from about 0.025 mm to about 0.10 mm.

2. The head according to claim 1, wherein the packing factor is within a range from about 45% to about 50%.

3. The head according to claim 1, wherein a plurality of tufts of the first type is arranged in a row at the inner portion of the head, and a plurality of tufts of the second type is arranged in a row at the outer rim of the head.

4. The head according to claim 1, wherein the radius of the concave curvature of the channel is within a range from about 0.03 mm to about 0.08 mm.

5. The head according to claim 1, wherein the cross-sectional area of each filament of the at least one tuft of the second type has an outer diameter within a range from about 0.15 mm to about 0.40 mm.

6. The head according to claim 1, wherein the cross-sectional area of each filament of the at least one tuft of the second type has an outer diameter, and each channel of the filaments of the at least one tuft of the second type has a concave curvature formed by neighboring and converging projections, the concave curvature having a radius, and the ratio of the outer diameter to the radius of the concave curvature of the channel is within a range from about 2.5 to about 12.

7. The head according to claim 1, wherein each projection of the cross-sectional area of the filaments of the at least one tuft of the second type is end-rounded thereby forming a curvature, the curvature having a diameter, and the diameter of the curvature of the projection is within a range from about 0.01 mm to about 0.04.

8. The head according to claim 1, wherein each projection of the cross-sectional area of the filaments of the at least one tuft of the second type is end-rounded thereby forming a curvature, the curvature having a diameter, and each channel of the filaments of the at least one tuft of the second type has a concave curvature formed by neighboring and converging projections, the concave curvature having a radius, and the ratio of the diameter of the curvature of the projection to the radius of the curvature of the channel is from about 0.2 to about 1.5.

9. The head according to claim 8, wherein the ratio of the diameter of the curvature of the projection to the radius of the curvature of the channel is from about 0.3 to about 1.0.

10. The head (14) according to claim 1, wherein each projection of the cross-shaped cross-sectional area of each filament of the at least one tuft of the second type tapers off in an outward direction.

11. The head according to claim 10, wherein each projection tapers off in the outward direction in an angle defined in a range from about 6° to about 25°.

12. The head according to claim 1, wherein each filament of the at least one tuft of the second type comprises along its longitudinal axis a substantially cylindrical portion and a tapered portion, the tapered portion tapers towards a free end of the filament, and the cylindrical portion has a cross-sectional area according to any of the preceding claims.

13. The head according to claim 1, wherein the tuft of the second type has a longitudinal axis and a cross-sectional area extending in a plane that is perpendicular to the longitudinal axis, and the plurality of filaments is arranged in a manner that the cross-sectional area of the tuft of the second type has a scaled up shape with respect to the shape of the cross-sectional area of each filament.

14. An oral care implement comprising the head according to claim 1.

* * * * *